United States Patent
Linz et al.

(10) Patent No.: US 7,728,134 B2
(45) Date of Patent: Jun. 1, 2010

(54) HYDRATES AND POLYMORPHS OF 4[[(7R)-8-CYCLOPENTYL-7-ETHYL-5,6,7,8-TETRAHYDRO-5-METHYL-6-OXO-2-PTERIDINYL]AMINO]-3-METHOXY-N-(1-METHYL-4-PIPERIDINYL)-BENZAMIDE, PROCESS FOR THEIR MANUFACTURE AND THEIR USE AS MEDICAMENT

(75) Inventors: Guenter Linz, Mittelbiberach (DE); Peter Sieger, Mittelbiberach (DE); Gerd F. Kraemer, Eberhardzell (DE); Rolf Herter, Biberach (DE); Matthias Hoffmann, Mittelbiberach (DE); Werner Rall, Mittelbiberach (DE); Rolf Schmid, Baltringen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 10 days.

(21) Appl. No.: 11/197,634

(22) Filed: Aug. 4, 2005

(65) Prior Publication Data
US 2006/0035902 A1    Feb. 16, 2006

(30) Foreign Application Priority Data
Aug. 14, 2004  (EP)  ................................. 04019366

(51) Int. Cl.
C07D 475/00  (2006.01)
A61K 31/519  (2006.01)

(52) U.S. Cl. ..................................... 544/258; 514/251
(58) Field of Classification Search .................. 514/251; 544/258
See application file for complete search history.

(56) References Cited

U.S. PATENT DOCUMENTS 4,957,922 A    9/1990   Lammens et al.

(Continued)

FOREIGN PATENT DOCUMENTS

CA    2458699    3/2003

(Continued)

OTHER PUBLICATIONS

Background Information for the Oct. 2002 ACPS Meeting, 11 pages.*

(Continued)

*Primary Examiner*—Mark L Berch
*Assistant Examiner*—Cecilia M Jaisle
(74) *Attorney, Agent, or Firm*—Michael P. Morris; Mary-Ellen M. Devlin; Anthony P. Bottino

(57) ABSTRACT

Disclosed are hydrates and polymorphs of 4-[[(7R)-8-cyclopentyl-7-ethyl-5,6,7,8-tetrahydro-5-methyl-6-oxo-2-pteridinyl]Amino]-3-methoxy-N-(1-methyl-4-piperidinyl)-benzamide:

(I)

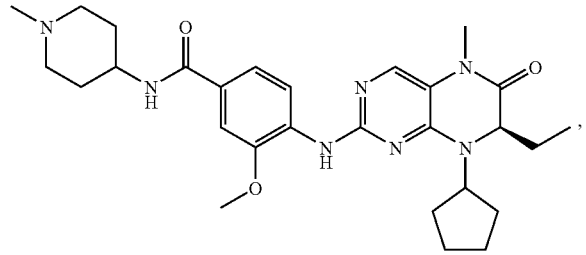

Figure 1A:
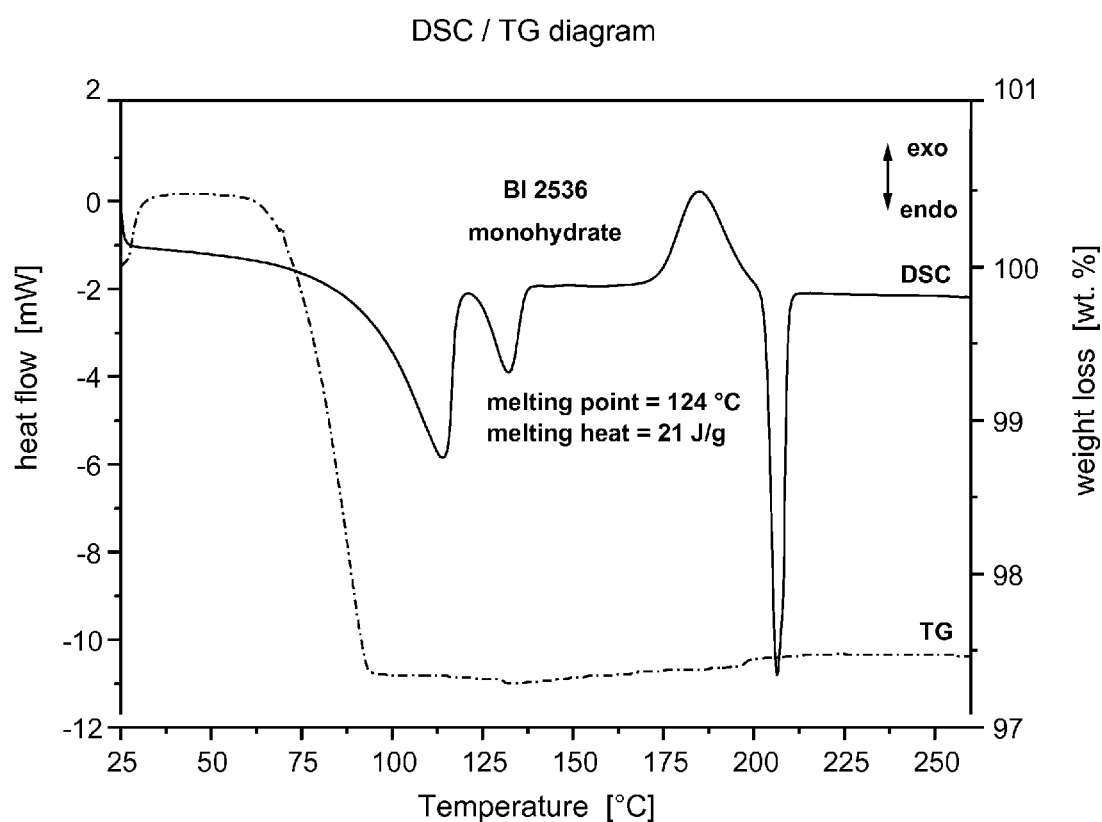

processes for preparing them and their use as pharmaceutical compositions with antiproliferative activity.

11 Claims, 8 Drawing Sheets

U.S. PATENT DOCUMENTS

| | | | |
|---|---|---|---|
| 5,167,949 | A | 12/1992 | Ferrand et al. |
| 5,424,311 | A | 6/1995 | Billhardt-Troughton et al. |
| 5,698,556 | A | 12/1997 | Grauert et al. |
| 6,174,895 | B1 | 1/2001 | Kleinman |
| 6,605,255 | B2 | 8/2003 | Kroll et al. |
| 6,806,272 | B2 | 10/2004 | Bauer et al. |
| 6,861,422 | B2 * | 3/2005 | Hoffmann et al. ......... 514/228.5 |
| 7,238,807 | B2 | 7/2007 | Duran et al. |
| 7,241,889 | B2 | 7/2007 | Hoffmann et al. |
| 7,332,491 | B2 | 2/2008 | Grauert et al. |
| 7,371,753 | B2 | 5/2008 | Stadtmueller et al. |
| 2002/0183292 | A1 | 12/2002 | Pairet et al. |
| 2002/0183293 | A1 | 12/2002 | Banerjee et al. |
| 2003/0130286 | A1 | 7/2003 | Denny et al. |
| 2004/0029885 | A1 | 2/2004 | Bauer et al. |
| 2004/0147524 | A1 | 7/2004 | Bauer et al. |
| 2004/0176380 | A1 | 9/2004 | Hoffmann et al. |
| 2005/0014760 | A1 | 1/2005 | Hoffmann et al. |
| 2005/0014761 | A1 | 1/2005 | Hoffmann et al. |
| 2005/0148501 | A1 | 7/2005 | Palmer et al. |
| 2005/0159414 | A1 | 7/2005 | Nickolaus et al. |
| 2005/0165010 | A1 | 7/2005 | Nickolaus et al. |
| 2006/0004014 | A1 | 1/2006 | Hoffmann et al. |
| 2006/0009457 | A1 | 1/2006 | Hoffmann et al. |
| 2006/0025411 | A1 | 2/2006 | Hoffmann et al. |
| 2006/0035902 | A1 | 2/2006 | Linz et al. |
| 2006/0035903 | A1 | 2/2006 | Mohr et al. |
| 2006/0046989 | A1 | 3/2006 | Grauert et al. |
| 2006/0047118 | A1 | 3/2006 | Stadtmueller et al. |
| 2006/0052383 | A1 | 3/2006 | Grauert et al. |
| 2006/0058311 | A1 | 3/2006 | Munzert et al. |
| 2006/0074088 | A1 | 4/2006 | Munzert et al. |
| 2006/0079503 | A1 | 4/2006 | Schwede et al. |
| 2008/0108812 | A1 | 5/2008 | Grauert et al. |
| 2008/0113992 | A1 | 5/2008 | Grauert et al. |
| 2008/0171747 | A1 | 7/2008 | Hoffman et al. |
| 2008/0177066 | A1 | 7/2008 | Linz et al. |
| 2008/0194818 | A1 | 8/2008 | Grauert et al. |
| 2008/0293944 | A1 | 11/2008 | Hoffmann et al. |
| 2008/0319190 | A1 | 12/2008 | Grauert et al. |
| 2009/0143379 | A1 | 6/2009 | Mohr et al. |

FOREIGN PATENT DOCUMENTS

| | | | |
|---|---|---|---|
| CA | 2517020 A1 | | 9/2004 |
| CA | 2517010 | | 11/2004 |
| CA | 2576290 A1 | | 2/2006 |
| EP | 143478 A1 | | 10/1984 |
| EP | 347146 A2 | | 6/1989 |
| EP | 399856 A1 | | 3/1990 |
| EP | 429149 A1 | | 11/1990 |
| ES | 2287583 | | 12/2007 |
| WO | 96/09045 A1 | | 3/1996 |
| WO | 96/34867 A1 | | 11/1996 |
| WO | 96/36597 A1 | | 11/1996 |
| WO | 98/11893 A1 | | 3/1998 |
| WO | 01/19825 A1 | | 3/2001 |
| WO | WO 01/19825 | * | 3/2001 |
| WO | WO 01/19825 A1 | | 3/2001 |
| WO | 01/70741 A1 | | 9/2001 |
| WO | 01/78732 | | 10/2001 |
| WO | 02/057261 A2 | | 7/2002 |
| WO | 02/076954 A1 | | 10/2002 |
| WO | 02/076985 A1 | | 10/2002 |
| WO | WO 03/020722 A1 | | 3/2003 |
| WO | 03/093249 A1 | | 11/2003 |
| WO | 2004/014899 A1 | | 2/2004 |
| WO | WO 2004/076454 | * | 9/2004 |
| WO | WO 2004/076454 A1 | | 9/2004 |
| WO | 2004093848 | | 11/2004 |
| WO | 2005/067935 A1 | | 7/2005 |
| WO | 2006/018182 | | 2/2006 |
| WO | 2006/018185 A2 | | 2/2006 |
| WO | 2006/018220 A2 | | 2/2006 |
| WO | 2006/018221 A1 | | 2/2006 |
| WO | 2006018221 | | 2/2006 |
| WO | 2006/021378 A1 | | 3/2006 |
| WO | 2007/090844 A1 | | 8/2007 |
| WO | 2009/019205 A1 | | 2/2009 |

OTHER PUBLICATIONS

Souillac, et al., Characterization of Delivery Systems, Differential Scanning Calorimetry, pp. 217-1 (in Encyclopedia of Controlled Drug Delivery, 1999, John Wiley & Sons, pp. 212-227).*

Wikipedia, Melting Point, Jan. 2007.*

Ghandi, L, et al., "An Open-Label Phase II Trial of the PLK Inhibitor BI 2536 in Patients with Sensitive Relapse Small Cell Lung Cancer". ASCO Meeting 2009.

ISR-01-1758.

BBC News/Health, Killer Breast Cancern Therapy Hope, www.newsvote.bbc/co./uk, downloaded Mar. 26, 2009.

Blain, S. W. et al., "Differential interaction of the cyclin-dependent kinase (Cdk) Inhibitor p27KIP with cyclin A-Cdk2 and cyclin D2-Cdk4". The Journal of Biological Chemistry, vol. 272, No. 41, Issue Oct. 10, 1997, pp. 25862-25872.

Leukemia & Lymphoma Society - Disease Information-Lymphoma. www.leukemia-lymphonna_org/all_page? item_id-7030, downloaded Mar. 26, 2009.

Leukemia & Lymphoma Society - Disease Information. www.leukemia-lymphoma.org/all_page?item_id-7026, downloaded Mar. 26, 2009.

MedlinePlus: Bacterial Infections. www.nim.nih.gov/medlineplus/print/bacterialinfections.htm, downloaded Mar. 26, 2009.

MedlinePlus: Viral Infections. www.nim.nih.gov/medlineplus/print/viralinfections.htm, downloaded Mar. 26, 2009.

National Kidney Foundation: Chronic Kidney Disease (CKD). www.kidney.org/kidneydisease/ckd/index.cfm, downloaded Mar. 26, 2009.

Viral Defense Foundation. www.viraldefense.org/mission.htm, downloaded Mar. 26, 2009.

Visiting Nurse Association of America. www.vnaa.org/gen/Germ_Protection_Center_Cold_and_Flu_Resources,html, downloaded Mar. 26, 2009.

Wagner, B. et al, "7-Benzylamino-6-chloro-2-piperazino-4-pyrrolidino-pteridine, a potent inhibitor of cAMP-specificphosphodiesterase, enhancing nuclear protein binding to the CRE consensus sequence in human tumour cells", Biochemical Pharmacology, Pergamon, Oxford, GB, pp. 659-668.

Organic Chemistry, Grupo Editorial Iberoamerica, Section 13, 3, pp. 301-302, 1983 (best copy available in Spanish).

Office Action mailed Apr. 28, 2004 for U.S. Appl. No. 10/374,876 filed Feb. 26, 2003 (Boehringer Ingelheim).

Office Action mailed Dec. 10, 2003 for U.S. Appl. No. 10/226,710 filed Aug. 23, 2002. (Boehringer Ingelheim).

ACPS Meeting, Background Information. "Scientific considerations of polymorphism in pharmaceutical solds: abbreviated new drug applications". Oct. 2002.

T. Ahlenius. "List of cardiovascular disorders/diseases". Ahlenius, Karolinska Institutet. Stockholm, Sweden. Cardiovascular Diseases, p1-34, Apr. 2007.

N. Ahmad. "Polo-like kinase (Plk) 1: a novel target for the treatment of prostate cancer". Dept of Dermatology, Univ. Wisconsin, pp. 3-5.

K. Arnold. "Collaboration to play key role in NCI's future, director says". Journal of the National Cancer Institute, Jun. 5, 2002, pp. 790-792, vol. 94, No. 11.

J. C. Bennett, et al., "Textbook of Medicine", Part XIV, Oncology, 1997.

Dipolar aprotic solvent. Exhibit A, IUPAC Compendium of Chemical Terminology, $2_{nd}$ Edition, 1997.

F. Z. Doerwald. "Side reactions in organice synthesis". 2005.

Eurasian Opinion, Appln No. 2007/00389/28, Maly Slatoustinsky per., d.10, kv.15, 101000 Moscow, Russia, "EVROMARKPAT", 2007.

G. Ferrand, et al., "Synthesis and potential antiallergic activity of new pteridinones and related compounds". Eur. J. Med. Chem, 31, 1996, pp. 273-280. XP-2246920.

D. Giron. "Thernal analysis and calorimetric methods in the characterization of plymorphs and solvates". Thermochimica Acta 248, 1995, pp. 1-59.

Goodman-Gilman's "The Pharmacological Basis of Therapeutics". Ninth edition, 1996, pp. 1225-1271.

Y. Ito, et al., "Polo-like kinase 1 (PLK) expression is associated with cell proliferative activity and cdc2 expression in malignant-lymphoma of the thyroid". Cat.Inist.Fr., 2006.

J. Jaworska, et al., "Review of methods for assessing the applicability domains of SARS and QSARS". Sponsor: the European Commission — Joint Research Ctr., Institute for Health and Consumer Protection —ECVAM, Italy, 2004.

M. K. Kashima, et al., "Expression of polo-like kinase (PLK1) in non-Hodgkin's lymphomas". NCBI, PubMed, 2005.

S.D. Kimball, et al., "Cell cycle kinases and checkpoint regulation in concern". Annual Reports in Medicinal Chemistry, 36, Chapter 14, pp. 139-148.

D. Marko, et al., "Intracellular localization of 7-benzylamino-6-chloro-2-piperazino-4-pyrrolidinopteridine in membrane structures impeding the inhibition of cytosolic cyclic AMP-specific phosphodiesterase". Biochemical Pharmacology, 63, 2002, pp. 669-676.

Y. Masuda, et al., "B-Hydroxyisovalerylshikonin induces apoptosis in human leukemia cells by inhibiting the activity of a polo-like kinase 1 (PLK)". 2003, Oncogene, 22, pp. 1012-1023.

Merck Manual of Medical Information. "Parasitic Infections". Chapter 184, 2003.

K. Mito, et al., "Expression of polo-like kinase (PLK1) in non-Hodgkin's lymphomas". NCBI, PubMed, 2005.

K. Nagao, et al., "Effect of MX-68 on airway inflammation and hyperresponsiveness in mice and guinea-pigs". Journal of Pharmacy and Pharmacology, JPP 2004, 56, pp. 187-196.

National Institute of Neurological Disorders, Index Stroke, 2006.

P. Norman. "PDE4 inhibitors". 1999, Ashley Publications Ltd., pp. 1101-1118.

Ohio Dept of Health, "Brain and Other Central Nervous System Cancer in Ohio, 1997-2001". Sep. 2004, pp. 1-4.

P.N. Rylander. "Hydrgenation Methods". 1985, Chapters 8, 9, 10, 11.

P.N. Rylander. "Hydrgenation Methods". 1985, Chapters 1, 2.

P.N. Rylander. "Hydrgenation Methods". 1985, Chapters 3, 4.

P.N. Rylander. "Hydrgenation Methods". 1985, Chapter 5, 6, 7.

P.N. Rylander. "Hydrgenation Methods". 1985, Chapter 13.

R. E. Santing, et al., "Brochodilatory and anti-inflammatory properties of inhaled selective phosphodiesterase inhibitors in a guinea pig model of allergic asthma". European Journal of Pharmacology, 429, 2001, pp. 335-344.

J. S. Snyder, et al., "Common bacteria whose susceptibility to antimicrobials is no longer predictable". NCBI, PubMed, 2000, J. Med. Liban, 48, pp. 208-214.

F. Savelli, et al., "Brochodilatory and anti-inflammatory properties of inhaled selective phosphodiesterase inhibitors in a guinea pig model of allergic asthma". European Journal of Pharmacology, 429, 2001, pp. 335-344.

P. Souillac, et al., "Characterization of delivery systems, differential scanning calorimetry". pp. 212-227.

A. M. Sugar, et al., "Comparison of three methods of antifungal susceptibility testing with the proposed NCCLS standard broth macrodilution assay: lack of effect of phenol red". Mycology, Diagn Microbiol. Infect. Dis. 1995, 21-pp. 129-133.

N. Takai, et al., "Polo-like kinases (PLKs) and cancer". Oncogene, 2005, 24, pp. 287-291.

R. E. Tenbrink, et al., "Antagonist, partial agonist, and full agonist imidazo[1,5-a]quinoxaline amides and carbamates acting through the BABA/Benzodiazepine receptor". J. Med. Chem. 1994, 37, pp. 758-768.

W.W.Turner, et al., "Recent advances in the medicinal chemistry of antifungal agents". Current Pharmacutical Design, 1996, 2, pp. 209-224.

E.W. Verschuren, et al., "The cell cycle and how it is steered by Kaposi's sarcoma-associated herpesvirus cyclin". Journal of General Virology, 2004, 85, pp. 1347-1361.

S. R. Vippagunta, et al., "Crystalline solids". Advanced Drug Delivery Reviews, 48, 2001, pp. 3-26.

T. Voskoglou-Nomikos, et al., "Clinical predictive value of the in vitro cell line, human xenograft, and mouse allograft preclinical cancer models". Clinical Cancer Research vol. 9, 2003, pp. 4227-4239.

G. Wagner, et al., "Synthesis of new phrido[3',2':4,5] thieno '3,2-d] 1,2,3-triazine derivatives as antianaphylactics". Biosciences Dept of the University of Leipzig, Pharmazie (Pharmacy), 48, 19923, vol. 7, pp. 514-518.

Webster's Comprehensive Dictionary, 1996, pp. 1013-1014.

Wikipedia. "Melting Point".

D. E. Wolf, et al., "The structure of rhizopterin". Contribution from the Research Labs of Merck and Co. Inc. Nov. 1947, vol. 69, pp. 2753-2759. XP002352205.

* cited by examiner

Figures

Figure 3a    DSC/TG Diagram
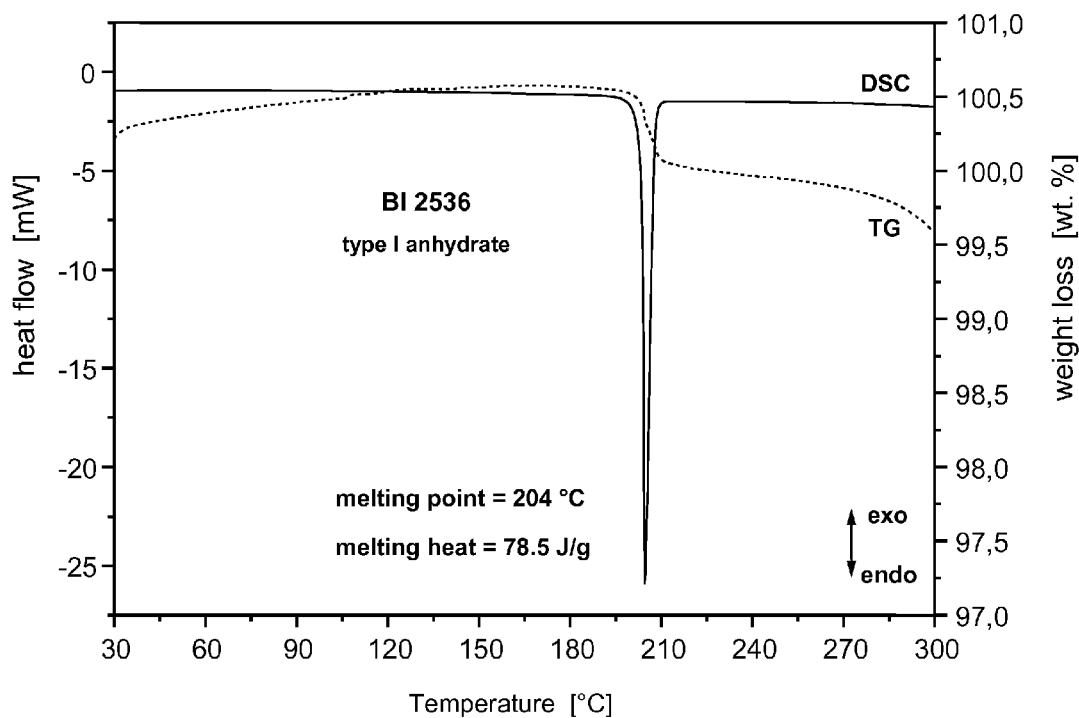

US 7,728,134 B2

HYDRATES AND POLYMORPHS OF 4[[(7R)-8-CYCLOPENTYL-7-ETHYL-5,6,7,8-TETRAHYDRO-5-METHYL-6-OXO-2-PTERIDINYL]AMINO]-3-METHOXY-N-(1-METHYL-4-PIPERIDINYL)-BENZAMIDE, PROCESS FOR THEIR MANUFACTURE AND THEIR USE AS MEDICAMENT

APPLICATION DATA

This application claims benefit to European Patent Application EP 04 019 366.6 Aug. 14, 2004.

FIELD OF INVENTION

The present invention relates to new hydrates and new polymorphs of the 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide, processes for preparing them and their use as pharmaceutical compositions.

BACKGROUND TO THE INVENTION

The compound 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide as a polo-like kinase (PLK) plays an important part in the regulation of the eukaryotic cell cycle.

The compound 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide has the structure of the following formula (I).

(I)

Similar dihydropteridinones are described in WO 03/020722.

BRIEF DESCRIPTION OF THE FIGS

FIG. 1a: Compound of the formula (I) monohydrate characterized by DSC/TG (Differential Scanning Calorimetry/Thermogravimetry).

Figure 1B:
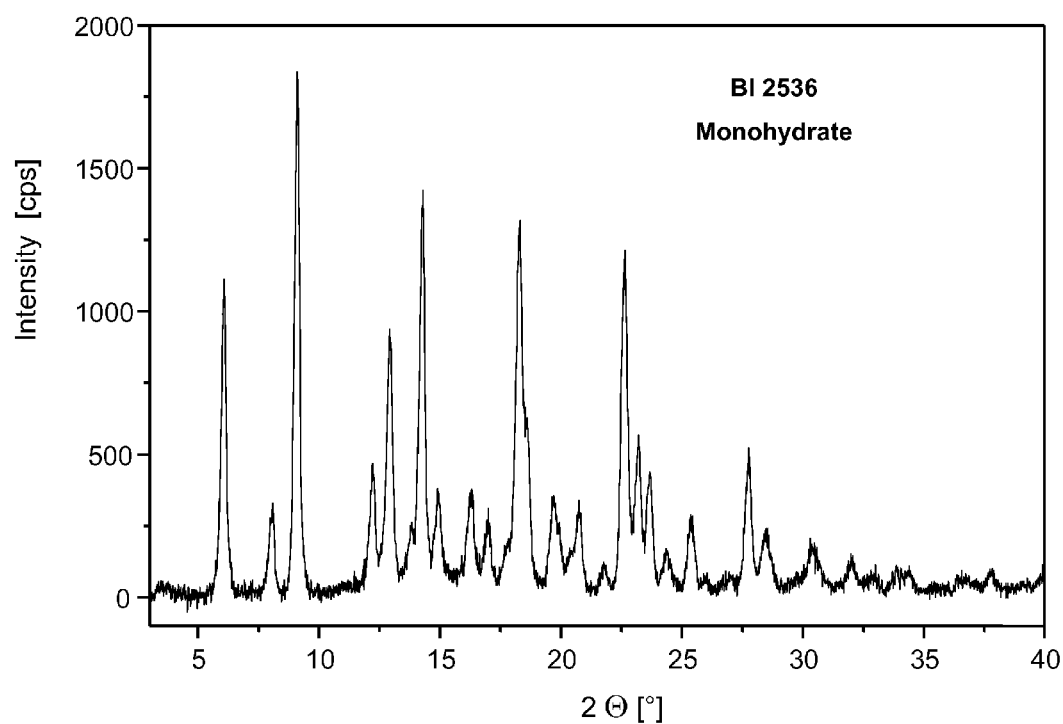

FIG. 1b: Compound of the formula (I) monohydrate characterized by X-ray powder diffraction.

Figure 2A:
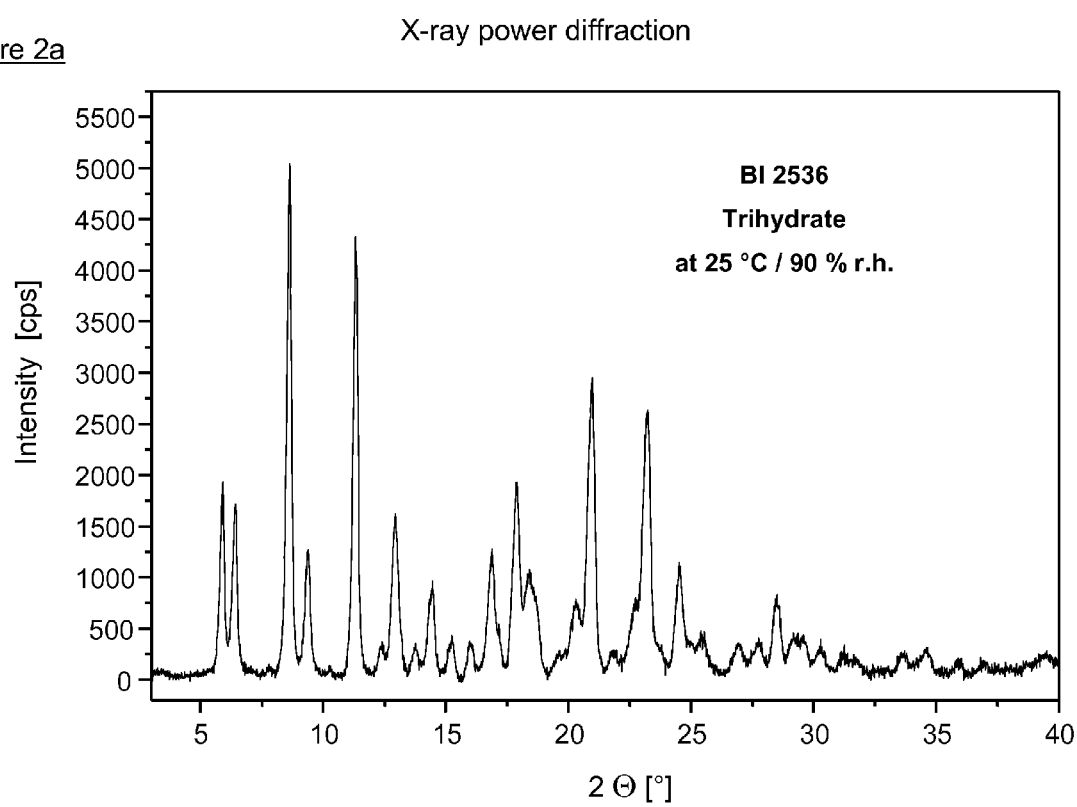

FIG. 2a: Compound of formula (I) Trihydrate characterized by X-ray powder diffraction.

FIG. 3a: Compound of formula (I) type I anhydrate characterized by DSC/TG (Differential Scanning Calorimetry/Thermogravimetry).

Figure 3B:
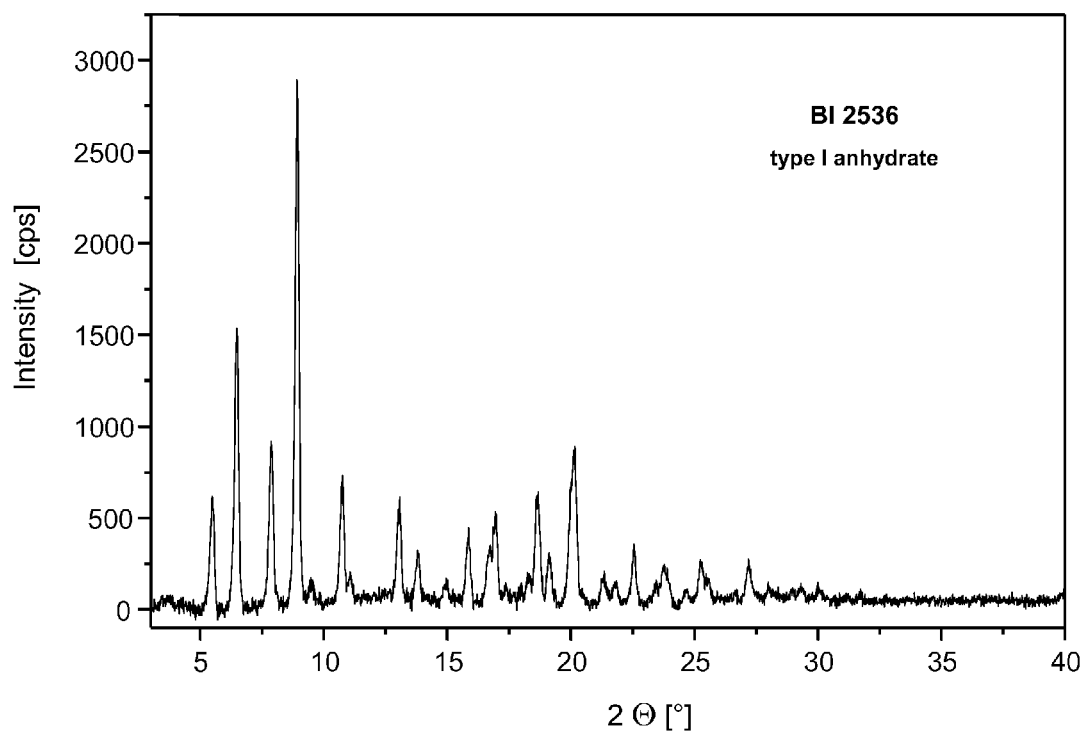

FIG. 3b: compound of formula (I) type I anhydrate characterized by X-ray powder diffraction.

Figure 4A:
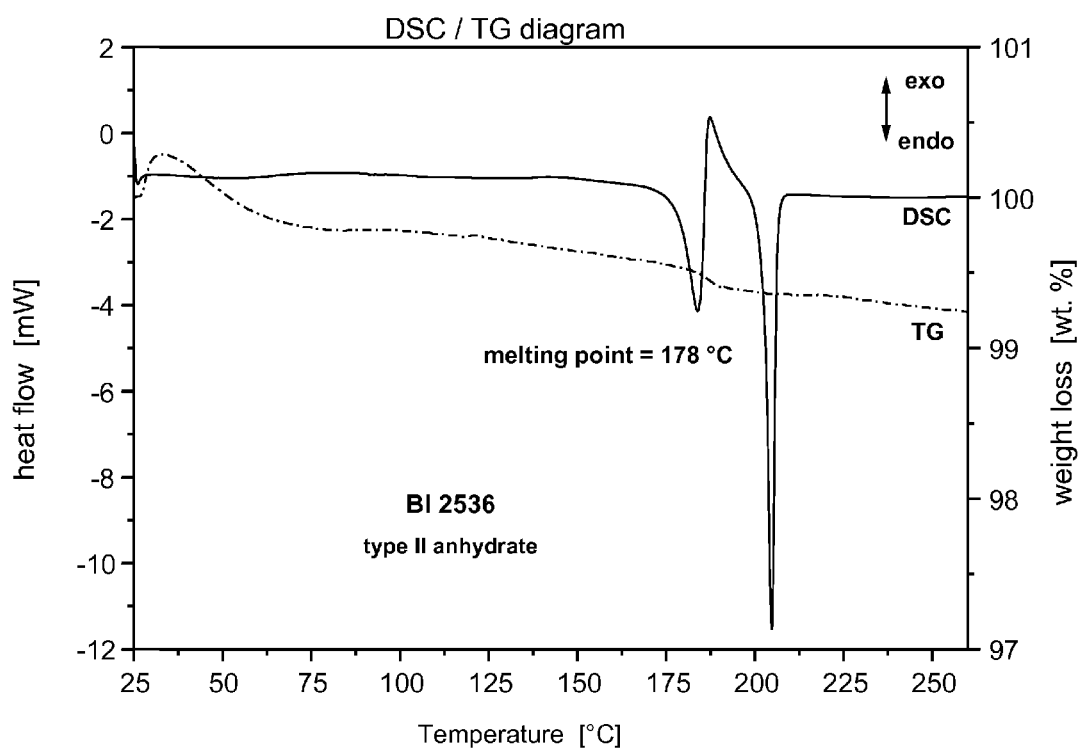

FIG. 4a: Compound of formula (I) type II anhydrate characterized by DSC/TG (Differential Scanning Calorimetry/Thermogravimetry).

Figure 4B:
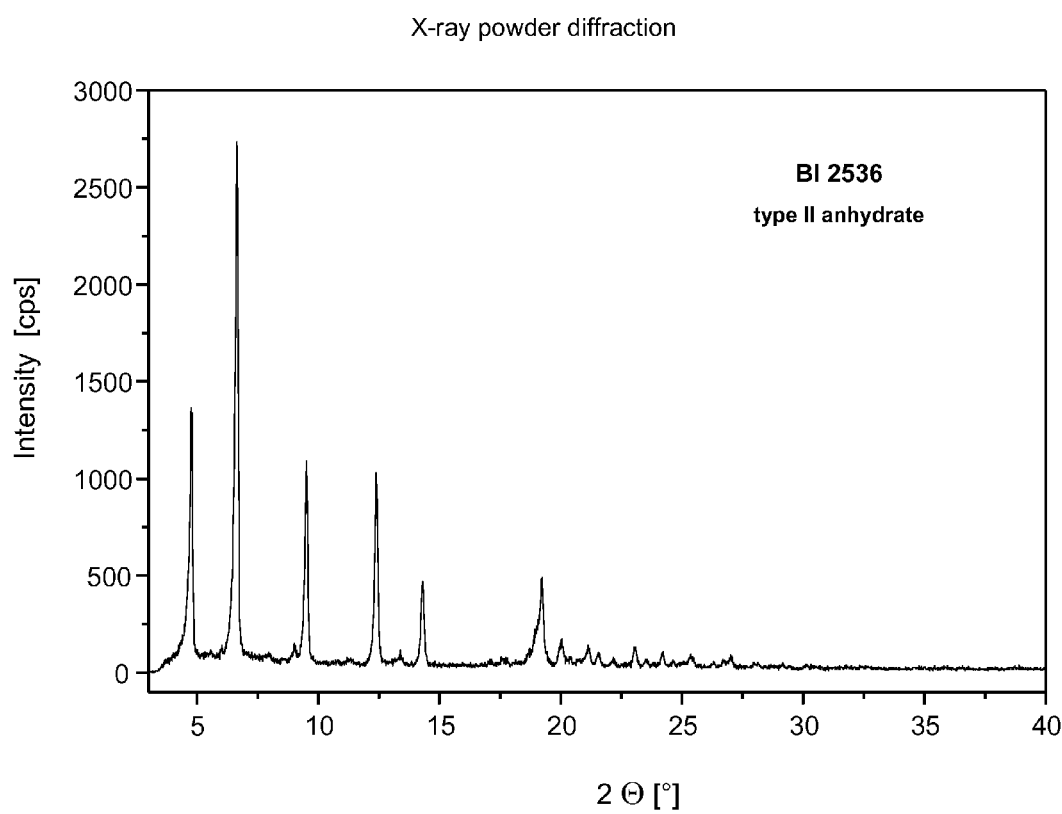

FIG. 4b: Compound of formula (I) type II anhydrate characterized by X-ray powder diffraction.

Figure 5A:
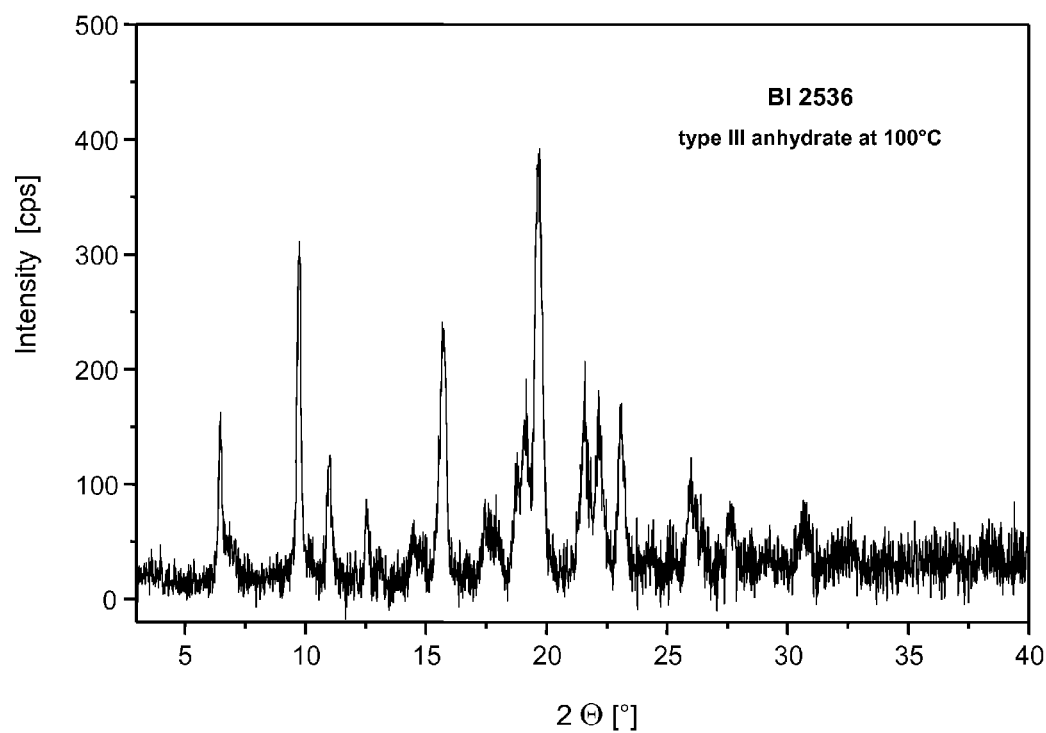

FIG. 5a: Compound of formula (I) type III anhydrate characterized by X-ray powder diffraction.

DETAILED DESCRIPTION OF THE INVENTION

The present invention provides new hydrates and new polymorphic forms of the compound of formula (I) with an antiproliferative activity.

It therefore relates to hydrates of the compound of formula (I):

(I)

The hydrate of the compound of formula (I) is preferred, which is the monohydrate.

Also preferred is the hydrate of the compound of formula (I), which is the trihydrate.

The invention further relates to the anhydrate of the compound of formula (I).

Also preferred is the anhydrate of the compound of formula (I), which is present as the type I anhydrate.

Also preferred is the anhydrate of the compound of formula (I), which is present as the type II anhydrate.

Also preferred is the anhydrate of the compound of formula (I), which is present as the type III anhydrate.

The invention further relates to a pharmaceutical composition which contains a therapeutically effective amount of one of the hydrates and polymorphic forms of the compound of formula (I) according to the invention described above and one or more pharmaceutically acceptable excipients.

The invention further relates to the hydrates and polymorphic forms of the compound of formula (I) according to the invention for use as pharmaceutical compositions with an antiproliferative activity.

The invention further relates to the use of the hydrates and polymorphic forms of the compound of formula (I) according to the invention for preparing a pharmaceutical composition for the treatment and/or prevention of cancer, infections, inflammatory and autoimmune diseases.

The invention further relates to the use of the hydrates and polymorphic forms of the compound of formula (I) according to the invention for preparing a pharmaceutical composition for inhibiting polo-like kinases.

It is preferred according to the invention to use the hydrates and polymorphic forms of the compound of formula (I) for preparing a pharmaceutical composition for inhibiting the polo-like kinase PLK-1.

It is particularly preferred to use the hydrates and polymorphic forms of the compound of formula (I) according to the invention, the active substance being administered orally, enterally, intravenously, peritoneally or by injection.

The invention further relates to a process for preparing the compound of formula (I), characterised in that a compound of formula 4

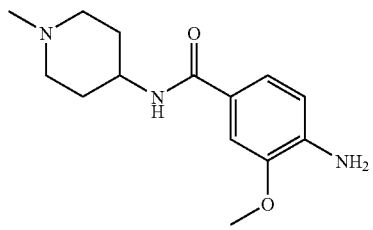

is reacted with a compound of formula 9,

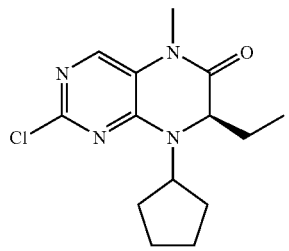

The invention further relates to a process for preparing a compound of formula 9,

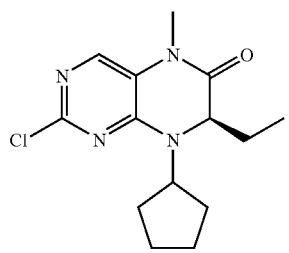

by methylation with dimethylcarbonate in the presence of a base at elevated temperature (between 80° C. and 180° C.), preferably at 130° C.

The invention further relates to a compound of formula 3

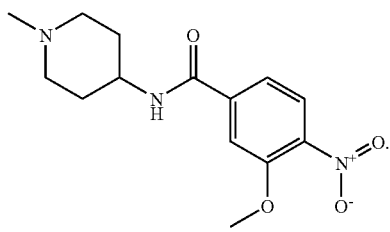

The invention further relates to compound of formula 4

The invention further relates to a process for preparing the monohydrate of the compound of formula (I), which comprises the following steps:
  (a) preparing a solution of the compound of formula (I), in a solvent mixture of isopropanol/water or acetone/water.
  (b) crystallising the monohydrate of the compound of formula (I) from the solvent mixture
  (c) isolating the monohydrate of the compound of formula (I).

The invention further relates to a process for preparing the trihydrate of the compound of formula (I), whereby the monohydrate of the compound of formula (I) is subjected to a relative humidity of at least 70%.

The invention further relates to a process for preparing the type III anhydrate of the compound of formula (I), wherein:
  (a) The monohydrate of the compound of formula (I) is rinsed with dry nitrogen, or
  (b) The monohydrate of the compound of formula (I) is subjected to a temperature of about 70° C., preferably 70 to 120° C., particularly preferably 70 to 90° C.

The invention further relates to a process for preparing the type I anhydrate of the compound of formula (I), whereby the type III anhydrate of the compound of formula (I) is melted and then the melt is crystallised at a temperature of at least 140° C., preferably from 140° C. to 160° C.

The invention further relates to a process for preparing the type I anhydrate of the compound of formula (I) comprising the following steps:
  a) preparing a solution of the compound of formula (I) in a solvent mixture of ethyl acetate and methyl-tert.-butylether, preferably in the ratio ethyl acetate/methyl-tert.-butylether of 3:5 (v/v) or a solvent mixture of methyl-isobutylketone/cyclohexane.
  b) crystallising the type I anhydrate of the compound of formula (I) from the solvent mixture and
  c) isolating the type I anhydrate of the compound of formula (I).

The invention further relates to a process for preparing the type II anhydrate of the compound of formula (I) comprising the following steps:
  a) preparing a solution of the compound of formula (I) in ethyl acetate,
  b) crystallising the type II anhydrate of the compound of formula (I) from ethyl acetate followed by the addition of diethyl ether and
  c) isolating the type II anhydrate of the compound of formula (I).

The invention further relates to a process for preparing the type I anhydrate of the compound of formula (I) comprising the following steps:
a) melting the type II anhydrate of the compound of formula (I),
b) crystallising the melt at a temperature of at least 185° C., preferably at a temperature of 185 to 200° C.

The compound of formula (I) may be prepared by the method of synthesis described hereinafter. The synthesis is shown in Diagram (1) and should be understood as illustrating the invention without restricting it to its contents.

Synthesis Plan 1

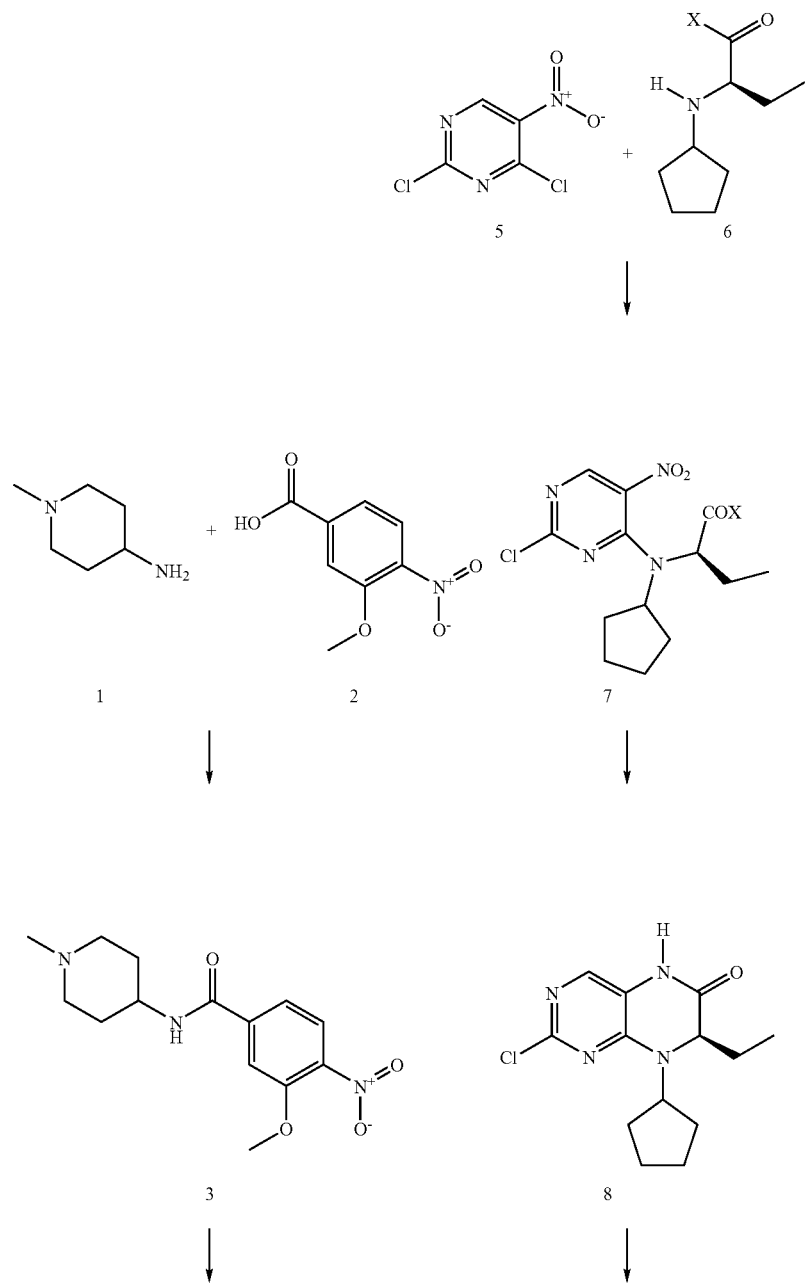

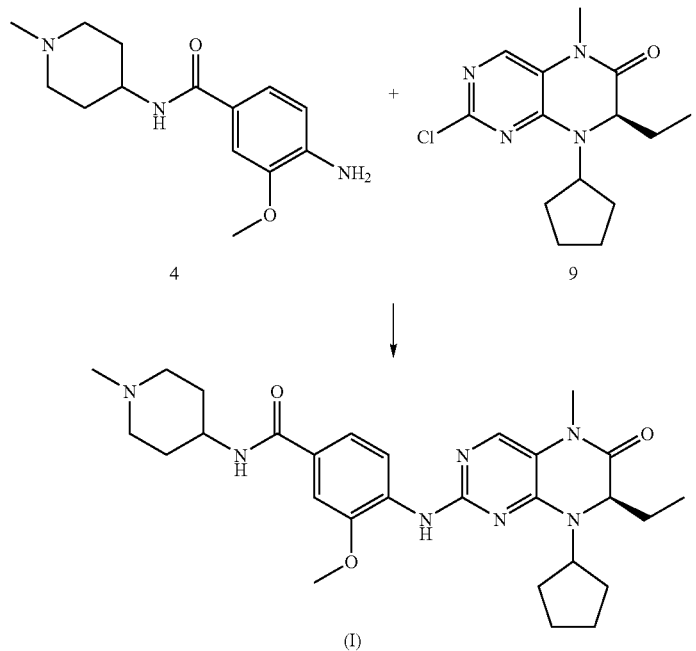

(I)

Preparation of the Aniline Fragment 4
Preparation of Compound 3

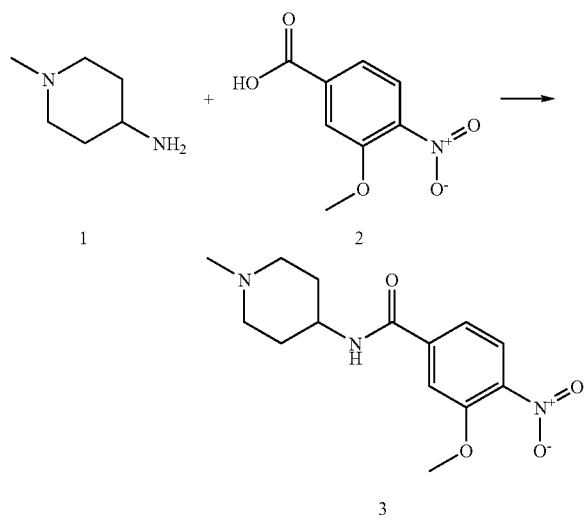

Variant 1A:

A suspension of 100 g (0.507 mol) of 3-methoxy-4-nitrobenzoic acid 2, 163 g (0.508 mol) O-(benzotriazol-1-yl)-N,N,N',N'-tetramethyluronium tetrafluoroborate and 192 mL (1.1 mol) ethyldiisopropylamine in 1.2 L dichloromethane is stirred for one hour at 25° C. 58 g (0.508 mol) 1-methyl-4-aminopiperidine 1 are added to the resulting solution and the mixture is stirred for 16 hours at 20° C. The solution is evaporated down to 600 mL and the organic phase is washed five times with 80 mL of 1 molar ammonia solution. The organic phase is concentrated by evaporation and the residue is chromatographed on silica gel using dichloromethane/methanol/conc. ammonia (15:1:0.1). Product fractions are combined, the solvent is evaporated off and the product is crystallised from ethyl acetate/methanol. 123 g of product 3 are obtained.

Variant 1B:

4.00 kg (20.3 mol) 3-methoxy-4-nitrobenzoic acid 2 are placed in 54 L toluene. 16 L toluene are distilled off under normal pressure. The mixture is cooled to 105° C. and 40 ml of dimethylformamide in 2 L toluene are added. At a jacket temperature of 120° C., 2.90 kg (24.3 mol) thionyl chloride are allowed to flow in within 30 min. and the mixture is rinsed with 4 L toluene. The reaction mixture is stirred for 1 hour at reflux temperature. Then 12 L toluene are distilled off under normal pressure. The contents of the reactor are cooled. A solution of 2.55 kg (22.3 mol) 1-methyl-4-aminopiperidine 1 in 2 L toluene and 2.46 kg (24.3 mol) triethylamine in 2 L toluene are allowed to flow in at 55-65° C. The mixture is rinsed with 4 L toluene. The suspension is stirred for 1 hour. 20 L of water are allowed to flow in and 3.08 kg (30.4 mol) conc. hydrochloric acid (36%) are added at 35-40° C. The mixture is rinsed with 2 L water. At 35-40° C. two phases are formed. The organic phase is separated off and the aqueous phase containing the product is returned to the reactor. It is rinsed with 4 L water. Under reduced pressure 3.2 L water are distilled off at 50° C. 4.87 kg (60.9 mol) sodium hydroxide solution (50%) are added to the remaining solution at 40° C. The mixture is rinsed with 4 L water. The product suspension is allowed to cool to 22° C. and stirred for 30 min. at this temperature. The suspension is suction filtered and the filter cake is washed with 40 L water. The product is dried at 40° C. in the vacuum drying cupboard. 5.65 kg of product are obtained.

Preparation of the Compound 4:

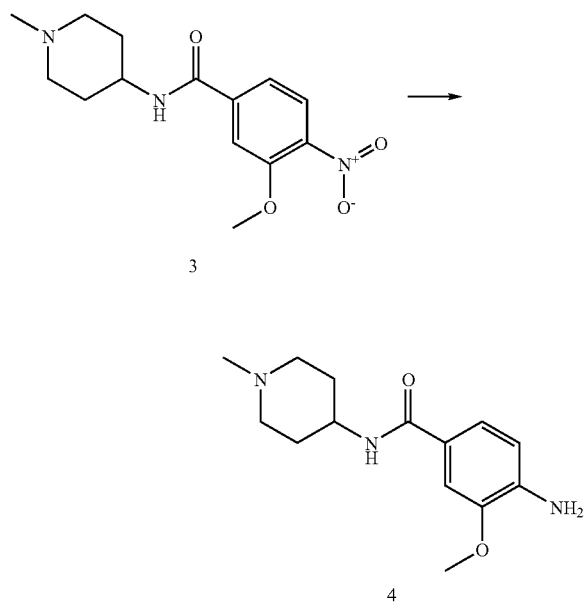

Variant 2A

A solution of 145 g (0.494 mol) 3 in 2 L methanol is hydrogenated at 4 bar in the presence of 2 g palladium on charcoal (10%). The catalyst is filtered off and the filtrate is concentrated by evaporation. 128 g product 4 are obtained.

Variant 2B

25 L demineralised water are added to 5.00 kg (17.0 mol) 3 and 600 g activated charcoal (industrial grade). Then 2.05 kg (34.1 mol) acetic acid are added. The suspension is stirred for 15 minutes at 22-25° C. 500 g of palladium on charcoal (10%) suspended in 3 L demineralised water are added and the mixture is rinsed with 2 L demineralised water. The contents of the reactor are heated to 40° C. and the mixture is hydrogenated at this temperature until the uptake of hydrogen ceases. The reaction mixture is filtered and the filter cake is washed with 10 L demineralised water. For crystallisation the filtrate is transferred into a reactor and the transporting container is rinsed with 5 L demineralised water. The reactor contents are heated to 50° C. A mixture of 5.45 kg (68.2 mol) sodium hydroxide solution (50%, industrial grade) and 7 L demineralised water is added. The mixture is stirred for 10 minutes at 45-50° C. The suspension is cooled to 20° C. and stirred for 1-1.5 hours at this temperature. The product is suction filtered, washed with 30 L demineralised water and dried at 45° C. in the vacuum drying cupboard. 4.13 kg of product 4 are obtained.

Preparation of the Dihydropteridinone Fragment 9

Preparation of the Amino Acid Esters 6a-d

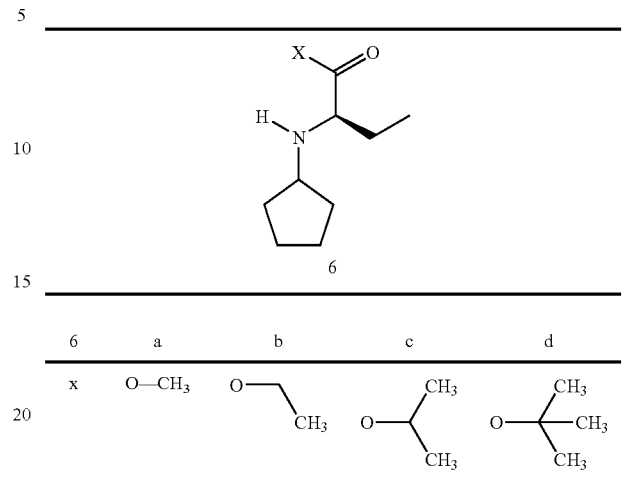

| 6 | a | b | c | d |
|---|---|---|---|---|
| x | O—CH$_3$ | O-CH$_2$CH$_3$ | O-CH(CH$_3$)$_2$ | O-C(CH$_3$)$_3$ |

The methyl ester 6a, ethyl ester 6b and 2-propyl ester 6c are prepared by methods described in the literature, for example according to WO 03/020722. The tert.-butyl ester 6d is prepared by transesterification with tert.-butyl acetate in the presence of perchloric acid (J. Med. Chem., Vol 37, No 20, 1994, 3294-3302).

The amino acids may be used in the form of the bases or as hydrochlorides in the following nucleophilic substitution reaction.

Preparation of the Amino Acid Amides 6e,f

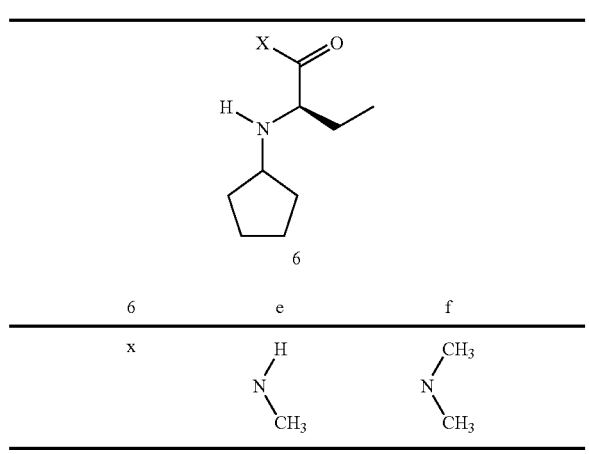

| 6 | e | f |
|---|---|---|
| x | NH-CH$_3$ | N(CH$_3$)$_2$ |

The amino acid amide 6e is prepared by aminolysis of the methyl ester 6a with 40% aqueous methylamine solution at ambient temperature.

The amino acid amide 6f is prepared by amide formation of the free amino acid with a five-fold excess of 2 molar dimethylamine solution in tetrahydrofuran in the presence of O-(benzotriazol-1-yl)-N,N,N',N'-tetramethyluronium tetrafluoroborate as coupling reagent.

Preparation of the Compounds 7

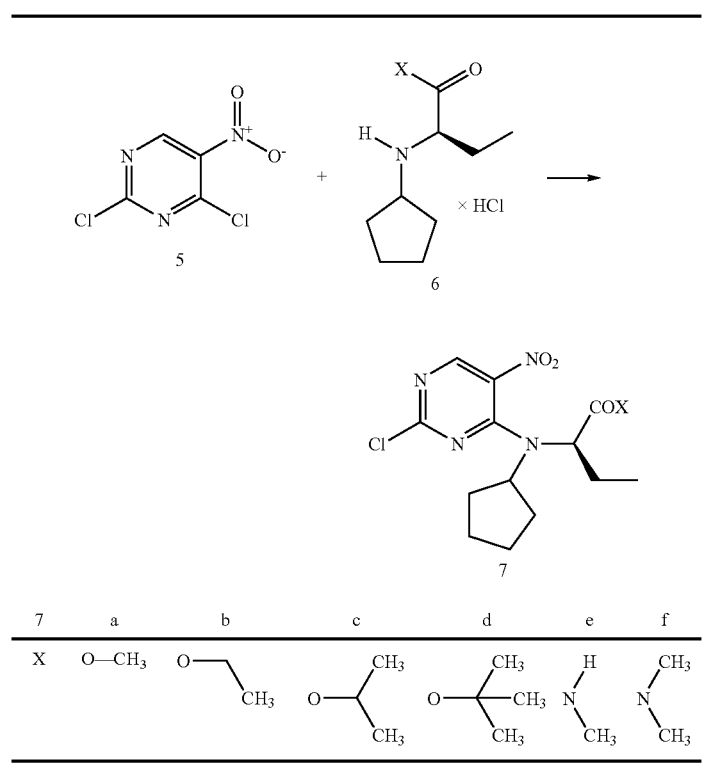

Preparation of the Methylester 7a

A suspension of 457 g (2.06 mol) of the amino acid methylester 6a and 693 g (8.25 mol) of powdered sodium hydrogen carbonate in 10 L cyclohexane is stirred for 15 minutes at ambient temperature. 440 g (2.27 mol) 2,4-dichloro-5-nitropyrimidine 5 and 1.5 L cyclohexane are added and the mixture is stirred for 3 days at ambient temperature. The reaction is monitored by HPLC. In order to redissolve any product which has crystallised out, 4 L of dichloromethane are added to the suspension. After the addition of 335 g magnesium sulphate the suspension is suction filtered and the inorganic filter cake is washed again with dichloromethane. The filtrate is evaporated down to 3.1 kg under reduced pressure and the suspension obtained is refluxed. The solution is allowed to cool slowly and stirred for one hour at 10-15° C. The suspension is suction filtered and the filter cake is washed with cyclohexane. The product is dried at 40° C. in the vacuum drying cupboard. 582 g of 7a (X═OCH₃) are obtained as a dark yellow solid.

Lipophilic solvents such as e.g. cyclohexane, methylcyclohexane, toluene and the mixtures thereof are particularly suitable for achieving high regioselectivity in the nucleophilic substitution in compound 5.

Compounds 7b-f are prepared analogously to this method. During the reaction of the amino acid amide 7e,f a fairly polar solvent such as e.g. ethyl acetate or dichloromethane is added to improve solubility.

Preparation of Compound 8

A freshly prepared suspension of 560 g (1.63 mol) 7a and 185 g Raney nickel in 2.8 L acetic acid is hydrogenated at 75° C. After the uptake of hydrogen has ended the catalyst is filtered off and the hydrogenation solution is evaporated down under reduced pressure. 4 L of demineralised water and 4 L ethyl acetate are added to the residue. A precipitate which contains the product is formed between the phases. The aqueous phase is separated off. 2 L ethyl acetate are added to the organic phase and the precipitate is suction filtered. The precipitate is suspended in 600 mL demineralised water, stirred for 1 hour at ambient temperature, suction filtered and washed with demineralised water. 110 g of moist product A are obtained.

The filtrate is washed three times with sodium chloride solution. The organic phase is concentrated by evaporation. 380 g of a reddish-brown residue B are obtained, which is combined with the moist product A. The combined crude products A and B are dissolved in 1.5 L ethanol at reflux temperature. The solution is filtered clear and the filter is rinsed with 150 mL ethanol. 550 mL demineralised water are added to the solution at reflux temperature. The mixture is left to cool and stirred for 16 hours at ambient temperature and for 3 hours at 0-5° C. The precipitate is suction filtered and washed with demineralised water/methanol (1:1) and then with demineralised water. The product is dried at 50° C. in the vacuum drying cupboard. 266 g product 8 are obtained as a solid.

Preparation of Compound 2 (Variant 3A)

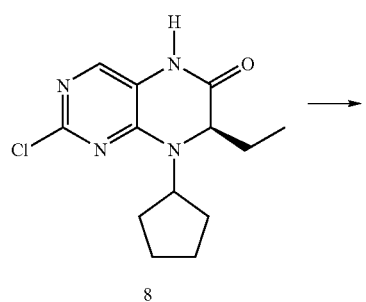

38 g (0.95 mol) sodium hydride (60% dispersion in mineral oil) are added batchwise to a solution of 264 g (0.94 mol) of 8 and 161 g (1.13 mol) methyl iodide in 2 L dimethylacetamide at 4-10° C. within one hour. The cooling bath is removed and the mixture is allowed to come up to 20° C. within 2 hours. It is cooled to 10° C. and a further 0.38 g (9.5 mmol) sodium hydride are added. The mixture is stirred for 4 hours at 10-15° C. 100 mL ethyl acetate and 1 kg ice are added to the reaction solution. The resulting suspension is diluted with 3 L demineralised water. The suspension is stirred for 2 hours, the precipitate is suction filtered and the filter cake is washed with demineralised water. The product is dried at 50° C. in the vacuum drying cupboard. 273 g of product 9 are obtained as colourless crystals.

Preparation of Compound 2 (Variant 3B)

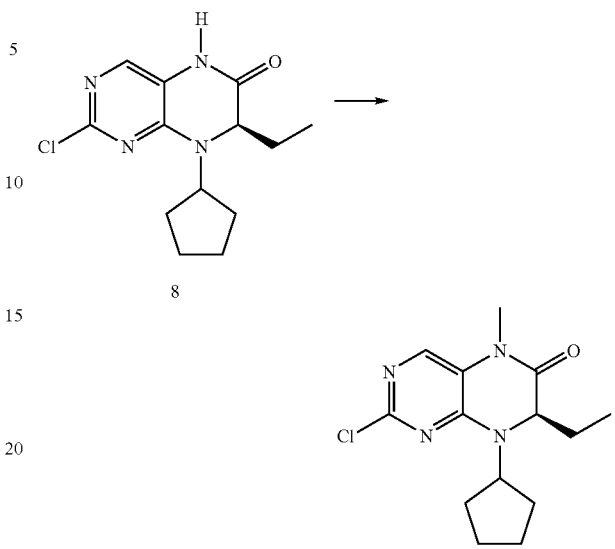

A suspension of 100 g (356 mmol) 8 and 73.8 g (534 mmol) potassium carbonate in 400 mL dimethylcarbonate is heated to 130° C. in an autoclave for 6 hours. The mixture is left to cool and 300 mL demineralised water and 200 mL ethyl acetate are added with stirring. The aqueous phase is separated off together with undissolved salts. 500 mL of solvent are distilled off from the organic phase at a pressure 180 mbar and a heating bath temperature of 70° C. 600 mL demineralised water are added to the residue and 100 mL solvent are distilled off at a pressure of 150 mbar and a heating bath temperature of 80° C. 350 mL ethanol are added to the suspension which is then heated to 65° C. The solution is left to cool and inoculated. It is cooled to 10° C., the precipitate is suction filtered and washed with a mixture of demineralised water and ethanol (2.5:1). The product is dried at 50° C. in the vacuum drying cupboard. 95.5 g product 2 are obtained.

Preparation of Compound of Formula (I)

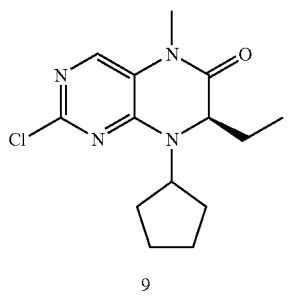

-continued

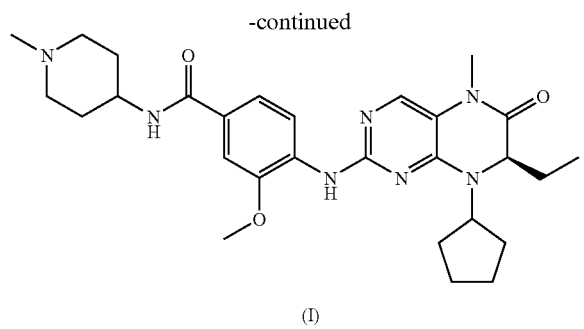

(I)

A suspension of 201 g (1.06 mol) para-toluenesulphonic acid-hydrate, 209 g (706 mmol) 9 and 183 g (695 mmol) 4 in 800 mL 2-methyl-4-pentanol is refluxed. 100 mL solvent are distilled off. The mixture is refluxed for 3 hours, 200 mL of 2-methyl-4-pentanol are added and 120 mL of solvent are distilled off. After 2 hours heating at reflux temperature a further 280 mL solvent are distilled off. The mixture is cooled to 100° C. and 1 L demineralised water and then 0.5 L ethyl acetate are added to the reaction solution. The organic phase is separated off and the aqueous phase is again washed with 0.5 L ethyl acetate. 1.5 L dichloromethane and 0.5 L ethyl acetate are added to the acidic aqueous phase. The pH value of the aqueous phase is adjusted to pH 9.2 with 260 mL of 6 normal sodium hydroxide solution. The aqueous phase is separated off and the organic phase is washed three times with in each case 1 L of 1 normal aqueous sodium hydrogen carbonate solution. The organic phase is dried over sodium sulphate, filtered and the solvent is evaporated down under reduced pressure. 406 g crude product are obtained.

The crude product is dissolved in 1.5 L ethyl acetate. At a temperature of 50-55° C. 2.5 L of methyl-tert.-butylether are added. The mixture is inoculated at 45° C. and stirred for 16 hours with cooling to ambient temperature. The suspension is stirred for 3.5 hours at 0-5° C. and the precipitate is suction filtered. The filter cake is washed again with methyl-tert.-butylether/ethyl acetate (2:1) and methyl-tert.-butylether. The product is dried at 50° C. in the vacuum drying cupboard. 236 g of crystalline product of the compound of formula (I) are obtained as the type I anhydrate.

Crystallisation:

46.5 g of the crystalline type I anhydrate described above are dissolved in 310 mL 1-propanol and filtered clear. The mixture is heated to 70° C. and 620 mL demineralised water are added. The solution is left cool to ambient temperature, cooled to 0-10° C. and seed crystals are added. The resulting suspension is stirred for 3 hours at 0-10° C. It is suction filtered and washed with cold 1-propanol/demineralised water (1:2) and demineralised water. The product is dried at 50° C. in the vacuum drying cupboard. 40.5 g crystalline product of the compound of formula (I) are obtained as the monohydrate.

The crude product of the reaction described above may also be crystallised directly as the crystalline monohydrate from 1-propanol/demineralised water.

The preparation of the hydrates and anhydrates of the compound of formula (I) may be carried out according to the following methods. These methods are shown in Diagram 2 and should be understood as illustrating the invention without restricting it to their content.

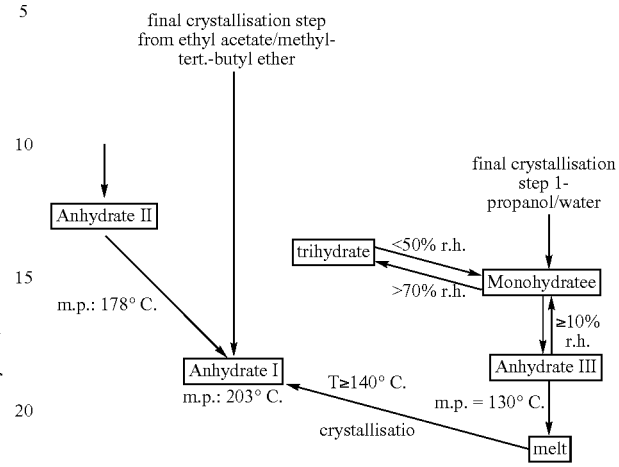

Diagram 2
Polymorphous characteristics of the compound of formula (I)

The hydrates and anhydrates according to the invention are characterised by DSC/TG (Differential Scanning Calorimetry/Thermogravimetry) and XRD (X-ray powder diffractograms) (Tables 1-5, FIGS. 1a to 5a).

All the XRD powder diffractograms were obtained using methods known in the art, by means of an X-ray powder diffractometer (Bruker D8 Advance). The diffractograms were obtained under the following measuring conditions: CuKα radiation ($\lambda$=1.5418 Å), 40 kV, 40 mA.

The DSC/TG measurements were carried out using equipment produced by the company Mettler Toledo (DSC 821 and TGA 851). The samples used were between 2 and 10 mg for DSC measurements and 10-30 mg for TG measurements. The heating rates were 10 K/min, and the measurements were carried out under an inert atmosphere (nitrogen flushing).

TABLE 1

X-ray powder reflections and their intensities (standardised) under normal ambient conditions of the monohydrate of the compound of formula (I)

| 2 Θ [°] | $d_{hkl}$ [Å] | intensity $I/I_o$ [%] |
|---|---|---|
| 6.07 | 14.54 | 62 |
| 8.06 | 10.96 | 15 |
| 9.11 | 9.7 | 100 |
| 12.23 | 7.23 | 24 |
| 12.93 | 6.84 | 50 |
| 13.81 | 6.41 | 13 |
| 14.29 | 6.2 | 76 |
| 14.94 | 5.92 | 18 |
| 16.29 | 5.44 | 18 |
| 17.01 | 5.21 | 15 |
| 17.8 | 4.98 | 8 |
| 18.29 | 4.85 | 69 |
| 18.6 | 4.77 | 32 |
| 19.71 | 4.5 | 18 |
| 19.94 | 4.45 | 13 |
| 20.43 | 4.34 | 7 |
| 20.76 | 4.27 | 17 |
| 21.8 | 4.07 | 5 |
| 22.64 | 3.92 | 65 |
| 23.21 | 3.83 | 29 |
| 23.67 | 3.76 | 22 |
| 24.38 | 3.65 | 7 |
| 25.4 | 3.5 | 14 |
| 25.98 | 3.43 | 2 |
| 27.01 | 3.3 | 3 |

TABLE 1-continued

X-ray powder reflections and their intensities (standardised) under normal ambient conditions of the monohydrate of the compound of formula (I)

| 2Θ [°] | $d_{hkl}$ [Å] | intensity $I/I_o$ [%] |
|---|---|---|
| 27.78 | 3.21 | 27 |
| 28.49 | 3.13 | 11 |
| 30.41 | 2.94 | 9 |

TABLE 2

X-ray powder reflections and their intensities (standardised) at ambient temperature and 90% r.h. of the trihydrate of the compound of formula (I)

| 2Θ [°] | $d_{hkl}$ [Å] | intensity $I/I_o$ [%] |
|---|---|---|
| 5.93 | 14.89 | 39 |
| 6.45 | 13.68 | 34 |
| 8.69 | 10.17 | 100 |
| 9.45 | 9.35 | 26 |
| 11.43 | 7.74 | 85 |
| 12.5 | 7.08 | 8 |
| 13.06 | 6.77 | 32 |
| 13.89 | 6.37 | 7 |
| 14.57 | 6.08 | 19 |
| 15.38 | 5.76 | 9 |
| 16.18 | 5.47 | 7 |
| 17.04 | 5.2 | 25 |
| 17.34 | 5.11 | 10 |
| 18.07 | 4.91 | 37 |
| 18.59 | 4.77 | 21 |
| 18.85 | 4.71 | 16 |
| 19.81 | 4.48 | 5 |
| 20.52 | 4.32 | 15 |
| 21.18 | 4.19 | 57 |
| 22.06 | 4.03 | 5 |
| 22.96 | 3.87 | 15 |
| 23.46 | 3.79 | 51 |
| 24.79 | 3.59 | 21 |
| 25.74 | 3.46 | 7 |
| 27.23 | 3.27 | 6 |
| 28.04 | 3.18 | 7 |
| 28.8 | 3.1 | 15 |
| 29.52 | 3.02 | 7 |
| 29.88 | 2.99 | 7 |
| 30.58 | 2.92 | 5 |

TABLE 3

X-ray powder reflections and their intensities (standardised) under normal ambient conditions of the anhydrate I of the compound of formula (I)

| 2Θ [°] | $d_{hkl}$ [Å] | intensity $I/I_o$ [%] |
|---|---|---|
| 5.48 | 16.11 | 22 |
| 6.47 | 13.65 | 51 |
| 7.88 | 11.21 | 31 |
| 8.93 | 9.89 | 100 |
| 9.5 | 9.31 | 5 |
| 10.74 | 8.23 | 22 |
| 11.06 | 7.99 | 5 |
| 13.06 | 6.78 | 19 |
| 13.81 | 6.41 | 9 |
| 14.95 | 5.92 | 4 |
| 15.86 | 5.58 | 14 |
| 16.71 | 5.3 | 10 |
| 16.94 | 5.23 | 17 |
| 18.27 | 4.85 | 5 |
| 18.65 | 4.75 | 20 |

TABLE 3-continued

X-ray powder reflections and their intensities (standardised) under normal ambient conditions of the anhydrate I of the compound of formula (I)

| 2Θ [°] | $d_{hkl}$ [Å] | intensity $I/I_o$ [%] |
|---|---|---|
| 19.14 | 4.63 | 9 |
| 20.12 | 4.41 | 29 |
| 21.32 | 4.16 | 5 |
| 21.81 | 4.07 | 4 |
| 22.57 | 3.94 | 11 |
| 23.44 | 3.79 | 4 |
| 23.78 | 3.74 | 7 |
| 24.66 | 3.61 | 3 |
| 25.28 | 3.52 | 7 |
| 25.55 | 3.48 | 4 |
| 27.21 | 3.27 | 8 |
| 28.03 | 3.18 | 2 |
| 29.35 | 3.04 | 3 |
| 30.04 | 2.97 | 3 |

TABLE 4

X-ray powder reflections and their intensities (standardised) under normal ambient conditions of the anhydrate II of the compound of formula (I)

| 2Θ [°] | $d_{hkl}$ [Å] | intensity $I/I_o$ [%] |
|---|---|---|
| 4.76 | 18.55 | 50 |
| 6.64 | 13.3 | 100 |
| 7.92 | 11.15 | 1 |
| 9.03 | 9.79 | 3 |
| 9.51 | 9.29 | 39 |
| 11.29 | 7.83 | 1 |
| 12.39 | 7.14 | 37 |
| 13.41 | 6.6 | 2 |
| 14.31 | 6.18 | 16 |
| 17.1 | 5.18 | 1 |
| 17.58 | 5.04 | 1 |
| 18.72 | 4.74 | 3 |
| 19 | 4.67 | 7 |
| 19.23 | 4.61 | 17 |
| 20.04 | 4.43 | 5 |
| 20.39 | 4.35 | 2 |
| 21.15 | 4.2 | 4 |
| 21.57 | 4.12 | 2 |
| 22.18 | 4 | 1 |
| 23.07 | 3.85 | 4 |
| 23.54 | 3.78 | 1 |
| 24.2 | 3.67 | 3 |
| 24.65 | 3.61 | 1 |
| 25.37 | 3.51 | 2 |
| 26.28 | 3.39 | 1 |
| 26.74 | 3.33 | 1 |
| 27.01 | 3.3 | 2 |
| 27.95 | 3.19 | 1 |
| 28.13 | 3.17 | 1 |

TABLE 5

X-ray powder reflections and their intensities (standardised) at 100° C. of the type III anhydrate of the compound of formula (I)

| 2Θ [°] | $d_{hkl}$ [Å] | intensity $I/I_o$ [%] |
|---|---|---|
| 6.49 | 13.61 | 41 |
| 9.74 | 9.07 | 81 |
| 10.99 | 8.04 | 29 |
| 12.56 | 7.04 | 21 |
| 14.44 | 6.13 | 13 |

TABLE 5-continued

X-ray powder reflections and their intensities (standardised)
at 100° C. of the type III anhydrate of the compound of formula (I)

| 2Θ [°] | $d_{hkl}$ [Å] | intensity $I/I_o$ [%] |
|---|---|---|
| 14.95 | 5.92 | 8 |
| 15.72 | 5.63 | 59 |
| 17.5 | 5.06 | 14 |
| 17.89 | 4.95 | 11 |
| 18.8 | 4.72 | 29 |
| 19.14 | 4.63 | 46 |
| 19.68 | 4.51 | 100 |
| 21.58 | 4.12 | 50 |
| 22.19 | 4 | 43 |
| 23.09 | 3.85 | 40 |
| 25.99 | 3.43 | 29 |
| 27.66 | 3.22 | 17 |
| 30.74 | 2.91 | 12 |

The anhydrate I, anhydrate II and monohydrate of the compound of formula (I) according to the invention may be used on their own or in conjunction with other active substances according to the invention, optionally also in conjunction with other pharmacologically active substances.

Suitable preparations include for example tablets, capsules, suppositories, solutions,—particularly solutions for injection (s.c., i.v., i.m.) and infusion—elixirs, emulsions or dispersible powders. The proportion of the pharmaceutically active compound(s) should be in the range from 0.01 to 90 wt.-%, preferably 0.1 to 50 wt.-% of the composition as a whole, i.e. in amounts which are sufficient to achieve the dosage range specified below. If necessary the doses specified may be given several times a day.

Suitable tablets may be obtained, for example, by mixing the active substance(s) with known excipients, for example inert diluents such as calcium carbonate, calcium phosphate or lactose, disintegrants such as maize starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral route, by injection or transdermally. For oral administration the tablets may of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The following examples of formulations illustrate the present invention without restricting its scope:

Examples of Pharmaceutical Formulations

| A) | Tablets | per tablet |
|---|---|---|
| | active substance | 100 mg |
| | lactose | 140 mg |
| | maize starch | 240 mg |
| | polyvinylpyrrolidone | 15 mg |
| | magnesium stearate | 5 mg |
| | | 500 mg |

The finely ground active substance, lactose and some of the maize starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance | 80 mg |
| | lactose | 55 mg |
| | maize starch | 190 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the maize starch, lactose, microcrystalline cellulose and polyvinylpyrrolidone are mixed together, the mixture is screened and worked with the remaining maize starch and water to form a granulate which is dried and screened. The sodium carboxymethyl starch and the magnesium stearate are added and mixed in and the mixture is compressed to form tablets of a suitable size.

| C) | Ampoule solution | |
|---|---|---|
| | active substance | 50 mg |
| | sodium chloride | 50 mg |
| | water for inj. | 5 ml |

The active substance is dissolved in water at its own pH or optionally at pH 3.5 to 6.5 and sodium chloride is added to make the solution isotonic. The resulting solution is filtered to remove pyrogens and the filtrate is transferred under aseptic conditions into ampoules which are then sterilised and heat-sealed. The ampoules contain 5 mg, 25 mg and 50 mg of active substance.

The invention claimed is:

1. A compound of formula (I):

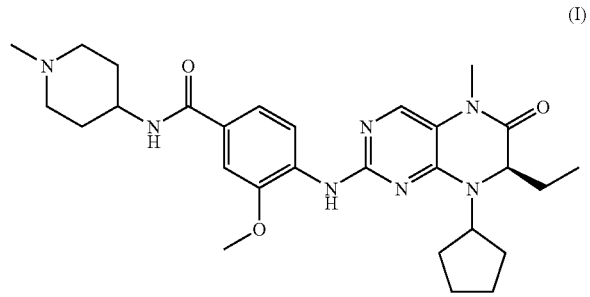

(I)

wherein the compound is a monohydrate or trihydrate.

2. The compound according to claim 1, wherein the compound is a monohydrate.

3. The compound according to claim 1, wherein the compound is a trihydrate.

4. A pharmaceutical composition, comprising a therapeutically effective amount of a hydrate of the compound of formula (I) according to claims 1, 2 or 3 and one or more pharmaceutically acceptable excipients.

5. A Process for preparing the monohydrate of the compound of formula (I) according to claim 2 comprising the following steps:

a) preparing a solution of the compound of formula (I) in a solvent mixture of 1-propanol or isopropanol and water,
b) crystallising the monohydrate of the compound of formula (I) from the solvent mixture and
c) isolating the monohydrate of the compound of formula (I).

6. The process for preparing the monohydrate of the compound of formula (I) according to claim 5, wherein in step a) the solvent mixture is 1-propanol and water.

7. A process for preparing the trihydrate of the compound of formula (I) according to claim 3, comprising subjecting a monohydrate of the compound of formula (I) to a relative humidity of at least 70%.

8. The compound according to claim 2, wherein the compound has the following X-ray powder reflections: d=14,54 Å, d=9,7 Å, d=6,2 Å, d=4,85 Å and d=3,92 Å, obtained under the following measuring conditions: CuKα radiation ($\lambda$=1.5418 Å), 40 kV, 40 mA.

9. The compound according to claim 8, wherein the compound has the following X-ray powder reflections and their intensities (standardized) under normal ambient conditions:

| 2Θ [°] | $d_{hkl}$ [Å] | intensity $I/I_o$ [%] |
|---|---|---|
| 6.07 | 14.54 | 62 |
| 8.06 | 10.96 | 15 |
| 9.11 | 9.7 | 100 |
| 12.23 | 7.23 | 24 |
| 12.93 | 6.84 | 50 |
| 13.81 | 6.41 | 13 |
| 14.29 | 6.2 | 76 |
| 14.94 | 5.92 | 18 |
| 16.29 | 5.44 | 18 |
| 17.01 | 5.21 | 15 |
| 17.8 | 4.98 | 8 |
| 18.29 | 4.85 | 69 |
| 18.6 | 4.77 | 32 |
| 19.71 | 4.5 | 18 |
| 19.94 | 4.45 | 13 |
| 20.43 | 4.34 | 7 |
| 20.76 | 4.27 | 17 |
| 21.8 | 4.07 | 5 |
| 22.64 | 3.92 | 65 |
| 23.21 | 3.83 | 29 |
| 23.67 | 3.76 | 22 |
| 24.38 | 3.65 | 7 |
| 25.4 | 3.5 | 14 |
| 25.98 | 3.43 | 2 |
| 27.01 | 3.3 | 3 |
| 27.78 | 3.21 | 27 |
| 28.49 | 3.13 | 11 |
| 30.41 | 2.94 | 9. |

10. The compound according to claim 3, wherein the compound has the following X-ray powder reflections: d=14,89 Å, d=10,17 Å, d=7,74 Å, d=4,19 Å and d=3,79 Å, obtained under the following measuring conditions: CuKα radiation ($\lambda$=1.5418 Å), 40 kV, 40 mA.

11. The compound according to claim 10, wherein the compound has the following X-ray powder reflections and their intensities (standardised) at ambient temperature and 90% relative humidity:

| 2Θ [°] | $d_{hkl}$ [Å] | intensity $I/I_o$ [%] |
|---|---|---|
| 5.93 | 14.89 | 39 |
| 6.45 | 13.68 | 34 |

-continued

| 2Θ [°] | $d_{hkl}$ [Å] | intensity $I/I_o$ [%] |
|---|---|---|
| 8.69 | 10.17 | 100 |
| 9.45 | 9.35 | 26 |
| 11.43 | 7.74 | 85 |
| 12.5 | 7.08 | 8 |
| 13.06 | 6.77 | 32 |
| 13.89 | 6.37 | 7 |
| 14.57 | 6.08 | 19 |
| 15.38 | 5.76 | 9 |
| 16.18 | 5.47 | 7 |
| 17.04 | 5.2 | 25 |
| 17.34 | 5.11 | 10 |
| 18.07 | 4.91 | 37 |
| 18.59 | 4.77 | 21 |
| 18.85 | 4.71 | 16 |
| 19.81 | 4.48 | 5 |
| 20.52 | 4.32 | 15 |

-continued

| 2Θ [°] | $d_{hkl}$ [Å] | intensity $I/I_o$ [%] |
|---|---|---|
| 21.18 | 4.19 | 57 |
| 22.06 | 4.03 | 5 |
| 22.96 | 3.87 | 15 |
| 23.46 | 3.79 | 51 |
| 24.79 | 3.59 | 21 |
| 25.74 | 3.46 | 7 |
| 27.23 | 3.27 | 6 |
| 28.04 | 3.18 | 7 |
| 28.8 | 3.1 | 15 |
| 29.52 | 3.02 | 7 |
| 29.88 | 2.99 | 7 |
| 30.58 | 2.92 | 5. |

\* \* \* \* \*